United States Patent [19]

Choi et al.

[11] Patent Number: 5,334,746
[45] Date of Patent: Aug. 2, 1994

[54] PROCESS FOR PRODUCING α-L-ASPARTYL-L-PHENYLALANINE METHYL ESTER

[75] Inventors: Kyung S. Choi; Dae K. Joo; Min S. Han; E Nam Hwang; Hong K. Choi, all of Seoul, Rep. of Korea

[73] Assignee: Miwon Co., Ltd., Rep. of Korea

[21] Appl. No.: 161,437

[22] Filed: Dec. 6, 1993

Related U.S. Application Data

[63] Continuation of Ser. No. 935,961, Aug. 27, 1992, abandoned.

[51] Int. Cl.$^5$ ............................................. C07C 229/00
[52] U.S. Cl. ........................................ 560/38; 560/41
[58] Field of Search .................................... 560/38, 41

[56] References Cited

U.S. PATENT DOCUMENTS

| | | | |
|---|---|---|---|
| 3,492,131 | 1/1970 | Schlarter | 99/141 |
| 3,786,039 | 1/1974 | Ariyoshi et al. | 260/112.5 |
| 4,071,511 | 1/1978 | Takemoto et al. | 260/112.5 |
| 4,680,403 | 7/1987 | Hisamitsu et al. | 546/247 |
| 4,684,745 | 8/1987 | Takemoto et al. | 560/41 |
| 4,760,164 | 7/1988 | Park et al. | 560/40 |

Primary Examiner—José G. Dees
Assistant Examiner—Samuel Barts
Attorney, Agent, or Firm—Birch, Stewart, Kolasch & Birch

[57] ABSTRACT

A process for the preparation of α-L-aspartyl-L-phenylalanine methyl ester in high yield, which comprises the steps of esterifying L-phenylalanine with methanol while undergoing continuous evaporation to remove the water formed during esterification, coupling the produced L-phenylalanine methyl ester with N-formyl-L-aspartic anhydride, deformylating the produced N-formyl-L-aspartyl-L-phenylalanine methyl ester, crystallizing the formed α-L-aspartyl-L-phenylalanine methyl ester as α-L-aspartyl-L-phenylalanine methyl ester hydrochloric acid salt, recovering the first α-L-aspartyl-L-phenylalanine methyl ester hydrochloric acid salt, esterifying α-L-aspartyl-L-phenylalanine in the filtrate to produce the second α-L-aspartyl-L-phenylalanine methyl ester, and combining the first and second α-L-aspartyl-L-phenylalanine methyl ester product.

26 Claims, 1 Drawing Sheet

PROCESS FOR PRODUCING α-L-ASPARTYL-L-PHENYLALANINE METHYL ESTER

This application is a continuation of application Ser. No. 07/935,961 filed on Aug. 27, 1992, now abandoned.

BACKGROUND OF THE INVENTION

1. Field of the Invention

The present invention relates to an improved process for producing L-phenylalanine methyl ester (hereinafter "PM") and α-L-aspartyl-L-phenylalanine methyl ester (hereinafter "α-APM"), and more particularly to, a process for the preparation of α-APM in high yield, which is a sweetening agent called "ASPARTAME."

2. Description of the Prior Art

There are many known large scale methods in the art for the production of α-APM using L-phenylalanine. For example, U.S. Pat. No. 3,786,039 discloses a method for the production of α-APM by the use of N-protected-L-aspartic anhydride and the lower alkyl ester of L-phenylalanine utilizing certain organic solvents. U.S. Pat. Nos. 4,071,511 and 4,684,745 disclose methods for the production of α-APM by the use of N-formyl aspartic anhydride and L-phenylalanine methyl ester to produce N-formyl-L-aspartyl-L-phenylalanine methyl ester and recovering the final product, α-APM, as the hydrochloric acid salt. U.S. Pat. No. 3,492,131 and U.S. Pat. No. 4,680,403 disclose methods for the production of PM by the use of sulfuric acid and hydrochloric acid, respectively, as the esterification catalyst. However, such prior art methods suffer from a number of disadvantages such as, for example, (a) they exhibit a lower yield; (b) since water is formed by esterification, this step takes a long time and produces an impure final product which contains, for example, α,β-L-aspartyl-L-phenylalanine dimethylester (hereinafter "α,β-MAPM"), by-product.

SUMMARY OF THE INVENTION

Accordingly, it is an object of the present invention to provide an improved process for producing α-APM in high yield, which eliminates the above disadvantages encountered with conventional methods.

Another object of the present invention is to provide a process for the preparation of PM, which includes the continuous water removal, e.g. by evaporation, in the esterification steps, for removing the formed water so as to shorten the reaction time and to achieve a high yield, and thereafter, the use of a methanolic base, in the neutralization steps, for reducing the hydrolysis of the L-phenylalanine methyl ester.

A further object of the present invention is to provide a process for the preparation of α-APM, which further includes the use of methanol, after deformylation with concentrated hydrochloric acid and water, for esterifying the remaining or untreated α-L-aspartyl-L-phenylalanine (hereinafter "α-AP") in the mother liquor, filtrate, so as to obtain a final product in high yield.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a process for the preparation of α-APM in high yield, which comprises the steps of esterifying L-phenylalanine with methanol while undergoing continuous evaporation to remove the water formed during esterification, coupling the produced PM with N-formyl-L-aspartic anhydride, deformylating the produced N-formyl-L-aspartyl-L-phenylalanine methyl ester, crystallizing the formed α-APM as α-L-aspartyl-L-phenylalanine methyl ester hydrochloric acid salt (hereinafter "α-APM.HCl"), recovering the first α-APM.HCl, esterifying α-AP in the mother liquor, filtrate, to produce the second α-APM products.

DESCRIPTION OF THE DRAWINGS

The present invention will become more fully understood from the detailed description hereinbelow and the accompanying drawings which are given by way of illustration only, and thus are not limitative of the present invention, and wherein.

PREFERRED EMBODIMENTS OF THE INVENTION

Figure 1:
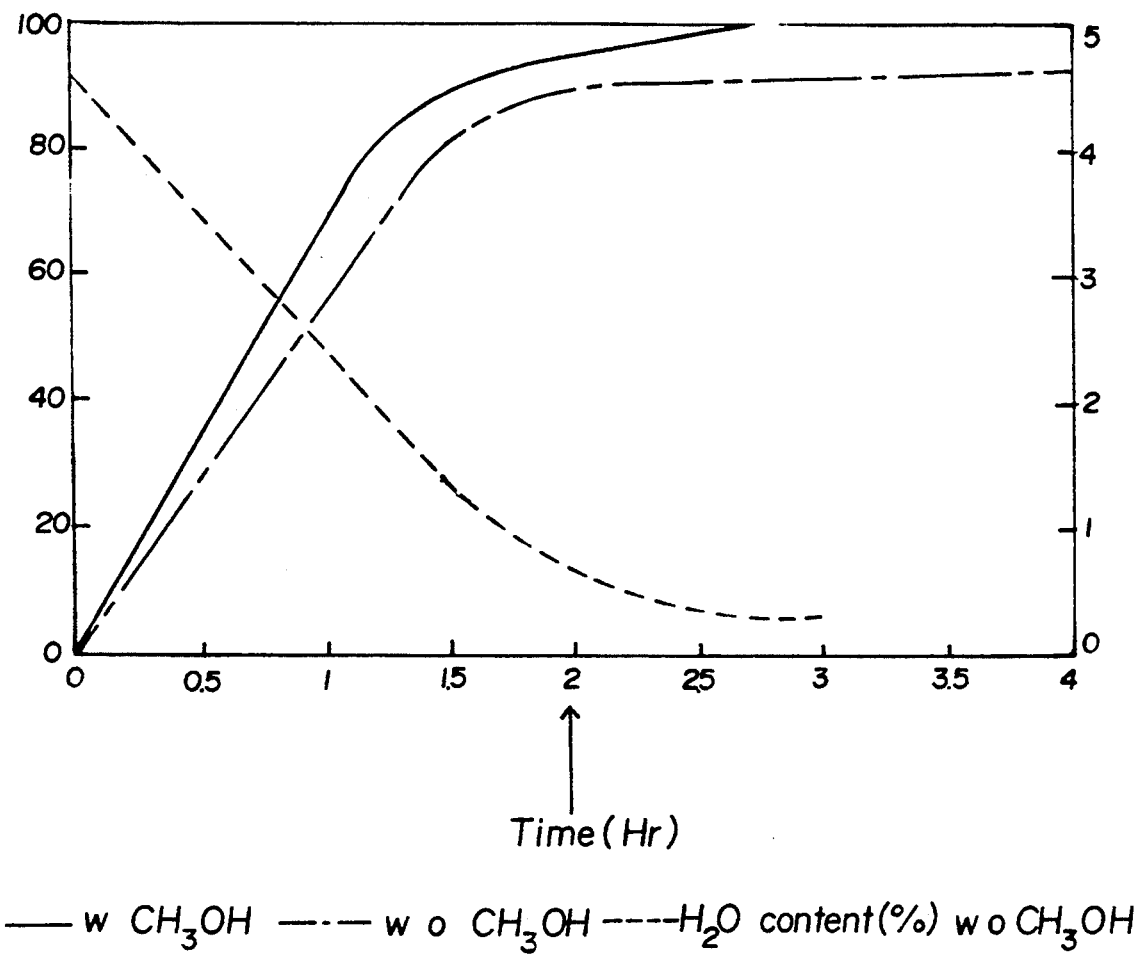
FIG. 1 illustrates the yield of the PM according to a quantity of the remaining water in the L-phenylalanine esterification step of the present invention —w/C-H₃OH, ——w/o CH₃OH, - - - H₂O content (%) w/ CH₃OH.

(A) Process for Preparing L-Phenylalanine Methyl Ester (PM)

U.S. Pat. Nos. 3,492,131 and 3,833,553 disclose methods for producing PM, which comprises the steps of preparing a PM.HCl salt, neutralizing the PM.HCl salt in an aqueous solution, and extracting PM with a water-immiscible organic solvent. Also, U.S. Pat. No. 4,680,403 discloses a method for producing PM, which comprises the steps of preparing a PM.H₂SO₄ salt, neutralizing the PM.H₂SO₄ salt in an aqueous alkaline solution, and extracting PM with a water-immiscible solvent.

However, the above-mentioned processes suffer from a number of disadvantages, such as for example, the esterification takes a long period of time and produces PM in low yields due to the presence of water formed in the reaction. Also, during neutralization of the PM salt, considerable hydrolysis of the PM cannot be avoided and the use of toluene as an extraction solvent causes environment pollution due to the effluence of toluene.

In the process for producing PM according to the present invention, L-phenylalanine (for example, 1 mole) is esterified with, for example, 200–1000 ml of anhydrous methanol and, for example, 1.0–2.0 mole of a strong acid, with the esterification being accompanied by continuous distillation in order to remove the water produced during esterification. Thus, the reaction temperature is maintained sufficiently high, for example 70° to 90° C., and the continuously fed methanol, for example 500 to 2000 ml, removes the water formed by the esterification reaction.

FIG. 1 shows the water content of condensed methanol evaporated and PM yield as a function of reaction time, when 1 mole of L-phenylalanine, 2 moles of H₂SO₄ and 300 ml of methanol are initially charged to the reactor, and methanol is continuously fed to the reactor when the reaction temperature is at about 70° to 90° C.

A methanolic base, such as sodium hydroxide dissolved in methanol, is utilized to neutralize the PM strong acid salt, followed by filtering the resulting salt, evaporating the methanol and adding a water-immiscible solvent, such as toluene, chloroform, methylene chloride, ethyl acetate, etc. as the reaction medium for the subsequent coupling reaction.

Because of the salt formed by using a methanolic base such as NaOH, KOH, MgO, and CaO, is practically insoluble in methanol, it can easily be removed from the solution by filtration. Therefore, the recovered and dried salt is sufficiently pure to be used or sold for other purposes. During neutralization of the acid salt PM.$H_2SO_4$, the PM hydrolysis is negligible and the yield from L-phenylalanine is nearly stoichiometric. By way of comparison, the prior art's utilization of an aqueous base, such as sodium carbonate solution, to neutralize the strong acid PM salts results in a 3 to 7% hydrolysis of PM.

Because of the removal of the water produced during esterification, the reaction time is reduced and the PM is produced in an increased yield. Also, in the present invention, the water-immiscible solvent is used as a reaction solvent for the coupling reaction whereas in the prior art the solvent is used as an extraction solvent.

(B) Process for Coupling α-L-Phenylalanine Methyl Ester with Formyl-L-Aspartic Anhydride The coupling reaction can be carried out utilizing conventional methods as in water-immiscible solvents which contain organic acid, for example, acetic acid, formic acid, etc. to produce N-formyl-α-L-aspartyl-L-phenylalanine methyl ester (hereinafter "α-FAPM").

(C) Process for Deblocking (Deformylation) and Recovery of α-APM

U.S. Pat. No. 4,684,745 discloses the use of aqueous methanol with HCl to remove the blocking group. Since methanol in the reaction medium can attack the free carboxyl group of the aspartic acid part of the α, β-APM, 5–10% of α,β-APM is consequently converted to α,β-L-aspartyl-L-phenylalanine dimethyl ester (hereinafter "α,β-MAPM"). The thus produced α,β-MAPM cannot be recovered, which remain as a loss. The yield of recovered α-APM.HCl crystals from α-FAPM is thus at a level of about 70–80%.

U.S. Pat. No. 4,071,511 discloses the use of water-immiscible organic solvents such as, for example, isopropanol, acetone, acetonitrile, etc. to avoid the formation of α,β-MAPM. However, 10–30% of the α-L-aspartyl-phenylalanine formed due to the hydrolysis of α-APM, cannot be converted to α-APM due to the absence of methanol. The yield of recovered α-APM.HCl crystals from α-FAPM is thus at a level of about 70%.

U.S. Pat. No. 4,173,562 discloses the use of HCl/$CH_3OH$/water to remove the formyl group from N-formyl-α-AP, to esterify and crystallize the resulting α-APM to α-APM.HCl. Also, U.S. Pat. No. 3,933,781 discloses the use of HCl/$CH_3OH$/water to esterify the α-AP to α-APM and crystallize the α-APM to α-APM.HCl.

However, the present invention relates to a process for producing α-APM.HCl, which further comprises the steps of removing the formyl group from the α-FAPM in HCl (about 5.5N)/water at a temperature of about 30° to 90° C., preferably about 45°–60° C. for about 30 minutes, cooling the medium to crystallize the formed α-APM.HCl, filtering and recovering the crystals. At this step, the formyl group of α-FAPM is completely removed. As the hydrochloric acid can partially hydrolyze the formed α-APM to α-AP by 30%, the mother liquor upon recovering the α-APM.HCl contains α-AP.

The present invention further involves the novel method for the recovery of α-AP, which comprises concentrating the mother liquor to give a final concentration of the α-AP of 20 to 30%, adding methanol and hydrochloric acid to give a final concentration of 20 to 30% and 5 to 10% respectively, in order to convert α-AP to α-APM and to crystallize the α-APM as α-APM.HCl. The reaction is carried out at 20° to 60° C. for 1 to 3 hours.

The adjustment of the concentration of α-AP is extremely important because if it is too low, the reaction efficiency becomes lowered, whereas if it is too high, a considerable side reaction may occur. The amount of methanol to be added is important as well because it may affect the formation of α-MAPM. Thus, the yield from α-FAPM is remarkably increased at a level of 85 to 89%.

The present invention will now be described in more detail in connection with the following examples which should be considered as being exemplary and not limiting of the present invention.

EXAMPLE 1

To a slurry of 165 g (1.0 mole) of L-phenylalanine in 500 ml $CH_3OH$, 111 ml of concentrated $H_2SO_4$ (97%, 2.0 mole) is added slowly maintaining the solution temperature of 30–°40° C. Then the solution is heated to 84°–86° C. To the solution, 1200 ml of $CH_3OH$ are fed for 3 hours while 1250 ml of vaporized aqueous $CH_3OH$ is removed from the reactor. The yield of obtained PM.$H_2SO_4$ is 99.8% based on L-phenylalanine as shown in the following Table 1.

TABLE 1

| Reaction (%) Time (hr) | PM YIELD % With $CH_3OH$ | PM YIELD % Without $CH_3OH$ | $H_2O$ Content with $CH_3OH$ |
| --- | --- | --- | --- |
| 0 | 0 | 0 | 4.5 |
| 0.5 | | | |
| 1.0 | 75 | 70 | 2.4 |
| 1.5 | 90 | 85 | 1.2 |
| 2.0 | 94 | 92 | 0.9 |
| 2.5 | 98.5 | 93 | 0.5 |
| 3.0 | 99.8 | 95 | 0.4 |
| 3.5 | | 96 | |
| 4.0 | | 95.5 | |

The prepared PM.$H_2SO_4$ solution is neutralized with 10% of methanolic-NaOH to form $Na_2SO_4$ crystals. The neutralized solution is then filtered and evaporated to remove the $CH_3OH$. To the concentrate, 760 ml of toluene is charged to solubilize the PM, hereafter the residual methanol is eliminated by evaporation. The final PM.toluene is analyzed by HPLC. The yield of PM is 98.7% based on PM.$H_2SO_4$ solution.

EXAMPLE 2

To 133 g of L-aspartic acid (1.0 mole), 84.5 g of 98% HCOOH, and 298.8 g of 97% acetic anhydride are added to react at 45°–50° C. for about 3.5 hours. The yield of formed N-formyl-L-aspartic anhydride is 98.8%. 45 ml thereof are evaporated at 40°–45° C. under a pressure of 100 torr. To the solution 30 ml of acetic acid and 100 ml of toluene are added to make a slurry. 940 ml of PM.toluene solution containing 179 g of PM prepared as in Example 1 is dropwisely added to the slurry which is maintained at a reaction temperature of 25°–30° C. for 30 minutes and then stirred for 30 minutes. The resulting solution is heated at 40° C. and stirred for another 30 minutes. The yield of α-FAPM is 82.8% and that of α-FAPM is 13.4%, resulting in the α/β ratio of 6.2.

EXAMPLE 3

1000 ml of PM.toluene solution containing 179 g of PM is dropwisely added to the slurry prepared in Example 2 and maintained, then stirred for 1 hour at about 25°–35° C. The yield of α-FAPM is 84.4% and the resulting α/β-ratio is 5.53.

EXAMPLE 4

To the slurry of α,β-FAPM containing 1 mole of α,β-isomer (α/β=5), 250 ml of concentrated HCl and 140 ml of water are added and the resulting solution is stirred for 45 minutes at 45° C. The solution is then cooled to 5° C. and stirred for 5 hours. The thus formed a-APM.HCl is filtered and recovered. The yield of α-APM.HCl.2H$_2$O is 70% (197.7 g) based on α-FAPM. The mother liquor is concentrated to 240 ml. Then to the concentrate is added 64 ml of methanol and 20 ml of concentrated hydrochloric acid. The solution is stirred for 1 hour at 45°–50° C. and then cooled to 5° C. and stirred for 2 days. The thus formed crystals are filtered and recovered. The total yield of α-APM.HCl.2H$_2$O is 88.8% (271.2 g) based on α-FAPM.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for producing L-phenylalanine methyl ester, comprising the steps of:
    (a) esterifying L-phenylalanine with methanol in the presence of a strong acid,
    (b) continuously removing the water produced during the esterification reaction to produce the L-phenylalanine methyl ester strong acid salt,
    (c) neutralizing said L-phenylalanine methyl ester strong acid salt with a base dissolved in methanol, which is substantially free of water, to produce a mixture, and
    (d) filtering said produced mixture and evaporating the methanol to produce concentrated L-phenylalanine methyl ester.

2. The process of claim 1, wherein said strong acid of step (a) is sulfuric acid.

3. The process of claim 1, wherein the water is removed by evaporation.

4. The process of claim 1, wherein said reaction of steps (a) and (b) is conducted at a temperature of about 70°–90° C.

5. The process of claim 4, wherein said reaction of steps (a) and (b) is conducted for 3 hours.

6. The process of claim 1, wherein for 1 mole of said L-phenylalanine, 200–1000 ml of said methanol and 1.0–2.0 mole of said strong acid are initially reacted and then about 500–2000 ml of methanol continuously added and methanol and water are removed therefrom.

7. The process of claim 1, wherein said base of step (c) is selected from the group consisting of NaOH, KOH, MgO, and CaO.

8. The process of claim 7, wherein the base is present in an amount of about 1 to 20% in the methanol.

9. A process for producing α-L-aspartyl-L-phenylalanine methyl ester, comprising the steps of:
    (a) dissolving L-phenylalanine methyl ester in a water-immiscible solvent selected form the group consisting of toluene, benzene, carbon tetrachloride, chloroform, methylene chloride, and ethyl acetate,
    (b) coupling L-phenylalanine methyl ester with N-formyl-L-aspartic anhydride in a said water immiscible solvent,
    (c) evaporating the coupling mixture to produce a crystal mixture,
    (d) adding concentrated hydrochloric acid and water to said crystal mixture for deformylating the N-formyl-L-aspartyl-L-phenylalanine methyl ester,
    (e) cooling and filtering the resulting mixture to produce a first crystal and a first filtrate,
    (f) concentrating said first filtrate to produce a concentrated first filtrate wherein α-L-aspartyl-L-phenylalanine is 20–40% by volume,
    (g) adding concentrated hydrochloric acid and methanol to said concentrated first filtrate to esterify α-L-aspartyl-L-phenylalanine and to produce α-L-aspartyl-L-phenylalanine methyl ester crystal as a second crystal product,
    (h) combining said first α-L-aspartyl-L-phenylalanine methyl ester crystal product and said second α-L-aspartyl-L-phenylalanine methyl ester crystal product, and
    (i) neutralizing with a base and filtering to produce α-L-aspartyl-L-phenylalanine methyl ester.

10. The process of claim 9, wherein said deformylation of step (c) is conducted at a temperature of 30°–90° C.

11. The process of claim 9, wherein said deformylation of step (c) is conducted with hydrochloric acid in an amount of 35% by volume and has a volume/weight ratio of 0.3–1, and said water has a volume/weight ratio of 0.3–2 based on the N-formyl-α-L-aspartyl-L-phenylalanine methyl ester.

12. The process of claim 9, wherein said added methanol and hydrochloric acid of step (f) are 20–30% and 5–10% of the final concentrate, respectively.

13. The process of claim 9, wherein said esterification of step (f) is conducted at a temperature of 20°–60° C.

14. A process for producing α-L-aspartyl-L-phenylalanine methyl ester, comprising the steps of:
    (a) esterifying L-phenylalanine with methanol in the presence of a strong acid,
    (b) continuously removing the water produced during the esterification reaction to produce the L-phenylalanine methyl ester strong acid salt,
    (c) neutralizing said L-phenylalanine methyl ester strong acid salt with a base dissolved in methanol, which is substantially free of water, to produce a mixture,
    (d) filtering said mixture and evaporating the methanol to produce a concentrate,
    (e) adding a water-immiscible solvent to dissolve said concentrate and form a solution of L-phenylalanine methyl ester, (f) adding said solution to N-formyl-L-aspartic acid anhydride and coupling said L-phenylalanine methyl ester with said N-formyl-L-aspartic anhydride, (g) evaporating the coupling mixture to produce a crystal mixture, (h) adding concentrated hydrochloric acid and water to said crystal mixture for deformylating the N-formyl-L-aspartyl-L-phenylalanine methyl ester, (i) cooling and filtering the resulting mixture to produce a first crystal and a first filtrate, (j) concentrating said first filtrate to produce concentrated first filtrate wherein α-L-aspartyl-L-phenylalanine is 20–40% by volume, (k) adding concentrated hydrochloric acid and methanol to said concentrated first filtrate to esterify α-L-aspartyl-L-phenylalanine therein to obtain a second α-L-aspartyl-L-phenylalanine methyl ester crystal product, (l) combining said first α-L-aspartyl-L-phenylalanine methyl ester crystal product and said second α-L-aspartyl-L-phenylalanine methyl ester crystal product, and (m) neutralizing with a base and filtering to produce α-L-aspartyl-L-phenylalanine methyl ester.

15. The process of claim 14, wherein said strong acid of step (a) is sulfuric acid.

16. The process of claim 15, wherein the water is removed by evaporization.

17. The process of claim 15, wherein said reaction of steps (a) and (b) is conducted at a temperature of about 70°–90° C.

18. The process of claim 17, wherein said reaction of steps (a) and (b) is conducted for 3 hours.

19. The process of claim 18, wherein for 1 mole of said L-phenylalanine, 200–1000 ml of said methanol and 1.0–2.0 mole of said strong acid are initially reacted and then about 500–2000 ml of methanol is continuously added and methyl alcohol and water are removed therefrom.

20. The process of claim 15, wherein said methanolic base of step (c) is selected from the group consisting of NaOH, KOH, MgO, and CaO.

21. The process of claim 20, wherein the methanolic base is present in an amount of about 1 to 20% in the methanol.

22. The process of claim 15, wherein said water-immiscible solvent of step (e) is selected from the group consisting of toluene, benzene, carbon tetrachloride, chloroform, methylene chloride, and ethyl acetate.

23. The process of claim 15, wherein said deformylation of step (h) is conducted at a temperature of 30°–90° C.

24. The process of claim 15, wherein said deformylation of step (h) is conducted with hydrochloric acid in an amount of 35% by volume and has a volume/weight ratio of 0.3–1, and said water has a volume/weight ratio of 0.3–2 based on N-formyl-α-L-aspartyl-L-phenylalanine methyl ester.

25. The process of claim 15, wherein said added methanol and hydrochloric acid of step (k) are 20–30% and 5–10% of the final concentrate, respectively.

26. The process of claim 15, wherein said esterification of step (k) is conducted at a temperature of 20°–60° C.

* * * * *

UNITED STATES PATENT AND TRADEMARK OFFICE
CERTIFICATE OF CORRECTION

PATENT NO. : 5,334,746
DATED : August 2, 1994
INVENTOR(S) : Kyung Sok CHOI et al.

It is certified that error appears in the above-identified patent and that said Letters Patent is hereby corrected as shown below:

In the Claims:

Claim 16, change "15" to --14--.

Claim 17, change "15" to --14--.

Claim 19, change "18" to --17--.

Claim 20, change "15" to --14--.

Claim 22, change "15" to --14--.

Claim 23, change "15" to --14--.

Claim 24, change "15" to --14--.

Claim 25, change "15" to --14--.

Claim 26, change "15" to --14--.

Signed and Sealed this

Eighteenth Day of October, 1994

Attest:

BRUCE LEHMAN

*Attesting Officer*  *Commissioner of Patents and Trademarks*